(12) United States Patent
Mott

(10) Patent No.: US 8,478,542 B2
(45) Date of Patent: Jul. 2, 2013

(54) NON-PARAMETRIC MODELING APPARATUS AND METHOD FOR CLASSIFICATION, ESPECIALLY OF ACTIVITY STATE

(75) Inventor: Jack E. Mott, Idaho Falls, ID (US)

(73) Assignee: Venture Gain L.L.C., Naperville, IL (US)

( * ) Notice: Subject to any disclaimer, the term of this patent is extended or adjusted under 35 U.S.C. 154(b) by 0 days.

(21) Appl. No.: 12/898,883

(22) Filed: Oct. 6, 2010

(65) Prior Publication Data

US 2011/0029250 A1    Feb. 3, 2011

Related U.S. Application Data

(63) Continuation of application No. 11/455,495, filed on Jun. 19, 2006, now Pat. No. 7,818,131.

(51) Int. Cl.
*G01N 33/48* (2006.01)

(52) U.S. Cl.
USPC .............................. 702/19; 600/300

(58) Field of Classification Search
USPC .............................. 702/19; 600/300
See application file for complete search history.

(56) References Cited

U.S. PATENT DOCUMENTS

| | | |
|---|---|---|
| 4,937,763 A | 6/1990 | Mott |
| 5,113,483 A | 5/1992 | Keeler et al. |
| 5,465,321 A | 11/1995 | Smyth |
| 5,479,574 A | 12/1995 | Glier et al. |
| 5,495,168 A | 2/1996 | Vries et al. |
| 5,526,446 A | 6/1996 | Adelson et al. |
| 5,539,638 A | 7/1996 | Keeler et al. |
| 5,574,387 A | 11/1996 | Petsche et al. |
| 5,640,103 A | 6/1997 | Petsche et al. |
| 5,682,317 A | 10/1997 | Keeler et al. |
| 5,774,379 A | 6/1998 | Gross et al. |
| 6,023,507 A | 2/2000 | Wookey |
| 6,108,616 A | 8/2000 | Borchers et al. |
| 6,110,214 A | 8/2000 | Klimasauskas |
| 6,246,972 B1 | 6/2001 | Klimasauskas |
| 6,278,962 B1 | 8/2001 | Klimasauskas et al. |
| 6,289,330 B1 | 9/2001 | Jannarone |
| 6,556,939 B1 | 4/2003 | Wegerich |
| 6,567,752 B2 | 5/2003 | Cusumano et al. |
| 6,616,613 B1 | 9/2003 | Goodman |
| 6,625,569 B2 | 9/2003 | James et al. |

(Continued)

OTHER PUBLICATIONS

Lester et al. "A Hybrid Discriminative/Generative Approach for Modeling Human Activities", International Joint Conference on Artificial Intelligence, pp. 1-7 2005.*

*Primary Examiner* — Max Hindenburg
*Assistant Examiner* — Renee Danega
(74) *Attorney, Agent, or Firm* — Fitch, Even, Tabin & Flannery LLP

(57) ABSTRACT

The activity state classification method of the present invention employs a kernel-based modeling technique, and more specifically a set of similarity-based models, which have been created using example data, to process an input observation or set of input observations, each comprising a set of sensor readings or "features" derived there from or other data, to predict the activity state of a person from whom the sensor data was obtained. A model is created for each class of activity. The input data is processed by each model and the resulting predictions are combined to yield a final prediction of which state of activity is represented by the input data.

19 Claims, 4 Drawing Sheets

U.S. PATENT DOCUMENTS

| | | |
|---|---|---|
| 6,678,639 B2 | 1/2004 | Little et al. |
| 6,826,552 B1 | 11/2004 | Grosser et al. |
| 6,853,920 B2 | 2/2005 | Hsiung et al. |
| 6,941,287 B1 | 9/2005 | Vaidyanathan et al. |
| 6,957,172 B2 | 10/2005 | Wegerich |
| 6,975,962 B2 | 12/2005 | Wegerich et al. |
| 7,027,953 B2 | 4/2006 | Klein |
| 7,308,385 B2 | 12/2007 | Wegerich et al. |
| 7,539,597 B2 | 5/2009 | Wegerich et al. |
| 7,640,145 B2 | 12/2009 | Wegerich et al. |
| 7,670,295 B2 | 3/2010 | Sackner et al. |
| 7,941,701 B2 | 5/2011 | Wegerich et al. |
| 8,200,321 B2 | 6/2012 | McCombie et al. |
| 8,290,129 B2 | 10/2012 | Rogers et al. |
| 8,290,730 B2 | 10/2012 | Watson et al. |
| 8,319,648 B2 | 11/2012 | Siejko et al. |
| 8,321,004 B2 | 11/2012 | Moon et al. |
| 2004/0127954 A1* | 7/2004 | McDonald, III ............ 607/48 |
| 2004/0152957 A1 | 8/2004 | Stivoric et al. |
| 2005/0246314 A1 | 11/2005 | Eder |
| 2006/0018516 A1 | 1/2006 | Masoud et al. |

\* cited by examiner

NON-PARAMETRIC MODELING APPARATUS AND METHOD FOR CLASSIFICATION, ESPECIALLY OF ACTIVITY STATE

CROSS REFERENCE TO RELATED APPLICATION

This application is a continuation of U.S. Non-Provisional patent application Ser. No. 11/455,495, filed Jun. 19, 2006, which claims benefit of priority under 35 U.S.C. §119(e) to U.S. Provisional Application Ser. No. 60/691,366 filed Jun. 17, 2006.

BACKGROUND OF THE INVENTION

1. Field of the Invention

The present invention relates generally to the field of classification. More particularly, the invention relates to classification based on data-driven techniques, especially classification of the state of activity of a person based on sensor readings.

2. Brief Description of the Related Art

One of the significant challenges in medical monitoring and testing of humans is posed by the need to measure and monitor humans in a consistent state, in order to draw conclusions from the measurements. For example, when measuring blood pressure to assess health, customary protocol dictates a person must be seated and resting for a period of minutes prior to taking the measurement, and the armband must be held out at heart level. When monitoring patients in an intensive care unit, patient movement is likely to often set off alarms on monitoring equipment, which works well only under extremely stable conditions. Measurements of patient vital signs need to be taken at appropriate conditions in order to optimally report the health of the patient. More broadly speaking, with the advent of wearable sensor technology for real-time monitoring of human health, it becomes imperative to filter down the collected data to only those measurements gathered during certain states of activity, to provide meaningful data.

Human activity classification also has important roles in other applications. Technology that monitors the wakefulness of a driver can aid in alerting the driver when they begin to doze off. Sensors may more appropriately convey the condition of a soldier in the battlefield if different states of activity can be discerned.

Determining the state of activity of a person based on sensor data poses a substantial problem of highly dynamic multivariate data. It is extremely difficult to come up with reliable means of determining the state of activity of a person. Mostly, rules are applied to raw data to determine activity state, but these rules can be difficult to apply across the variety of personal weight, height, and other differences. What is needed is a reliable way of determining activity state from the sensor data obtained from a subject human.

SUMMARY OF THE INVENTION

The present invention provides a novel method and apparatus for classification of a system based on data from the system, and more particularly classification of the activity state of a person based on sensor data from that person. Furthermore, it provides a comparatively autonomous means of classification that does not require great expertise on the part of the human user, nor does it require an impractical amount of computational power.

According to the invention, a learned set of data and associated classifications such as activity state known for that learned data is used to create a model or set of models that collectively provide classification of new observed data for which the classification is sought. For example, data may comprise snapshots of observed sensor data from one or more sensors on a person that measure parameters related to the person's activity or condition. The new data is processed real-time if desired, and the model or set of models classifies the new data with the recognized activity state or classification.

The invention utilizes similarity-based modeling to provide an output of the classification based on the modeling of the input data. The inventors have found similarity-based modeling shows general classification modeling capability and particular efficacy in modeling difficult, multivariate distinctions, such as that posed by activity state classification.

The inventive system can comprise software running on a computer, which can provide its classification result as an output to a screen or other indicator device, or as an input to further downstream processing that relies on the classification result. The software implementation of the invention can run on a personal computer-type or more powerful system, or can be embedded into onboard code in an appliance, handheld device, implantable, or remote autonomous device. In one embodiment, a separate modeling environment is provided for that permits computer-based learning, and downloading of the results into an embeddable form.

BRIEF DESCRIPTION OF THE DRAWINGS

The novel features believed characteristic of the invention are set forth in the appended claims. The invention itself, however, as well as the preferred mode of use, further objectives and advantages thereof, is best understood by reference to the following detailed description of the embodiments in conjunction with the accompanying drawings, wherein:

DETAILED DESCRIPTION OF THE PREFERRED EMBODIMENTS

The activity state classification method of the present invention employs a kernel-based modeling technique, and more specifically a set of similarity-based models, which have been created using example data, to process an input observation or set of input observations, each comprising a set of sensor readings or "features" derived there from or other data, to predict the activity state of a person from whom the sensor data was obtained. A model is created for each class of activity. The input data is processed by each model and the resulting predictions are combined to yield a final prediction of which state of activity is represented by the input data.

According to the invention, the kernel-based models can be of two forms. In the first form, the model has been created using data from the class of activity represented by that model, as well as data that represents the entire variety of other classes of activity that are possibly exhibited. Each model then further predicts whether the input data is representative of the class of data that model represents, by making an inferential class prediction of "in class" versus "not in class" (which is typically a prediction over the range of zero to one, where zero represents not in class, and one represents in-class). The inferential predictions of class are compared and the model/class with the output having the greatest confidence is designated as the class of the input. There are a number of methods for comparing these inferential outputs and for determining "confidence" detailed herein below. According to a second form, the model has been created only using data from the class of activity represented by that model. Each model then generates an autoassociative estimate of the parameters in the input data, that is, for each data value in the multivariate input observation, the model estimates a data value. The estimated multivariate observation is compared to the input observation, using a similarity operation or some other measure of likeness. The degree of similarity between the estimate and the actual input observation is used as a confidence that the input represents that state of activity. The outputs of each of the models for all the activity states are then compared to determine which is most likely the true class of the input observation, and that class is then designated as the class of the input.

The activity state of a human, or more broadly the condition of a human, can be determined in the present invention from data generated by sensors. Such sensors include accelerometers attached to a person, for example at the arms and/or legs; temperature sensors attached at the skin, or even surgically inserted; heart rate sensors; respiration measuring devices; respiration gas analysis sensors; embedded blood analysis sensors; blood pressure sensors; blood oxygen or blood gas sensors; skin and flesh conductivity sensors; eye scanning imaging hardware; sweat sensors; and the like.

Figure 1:
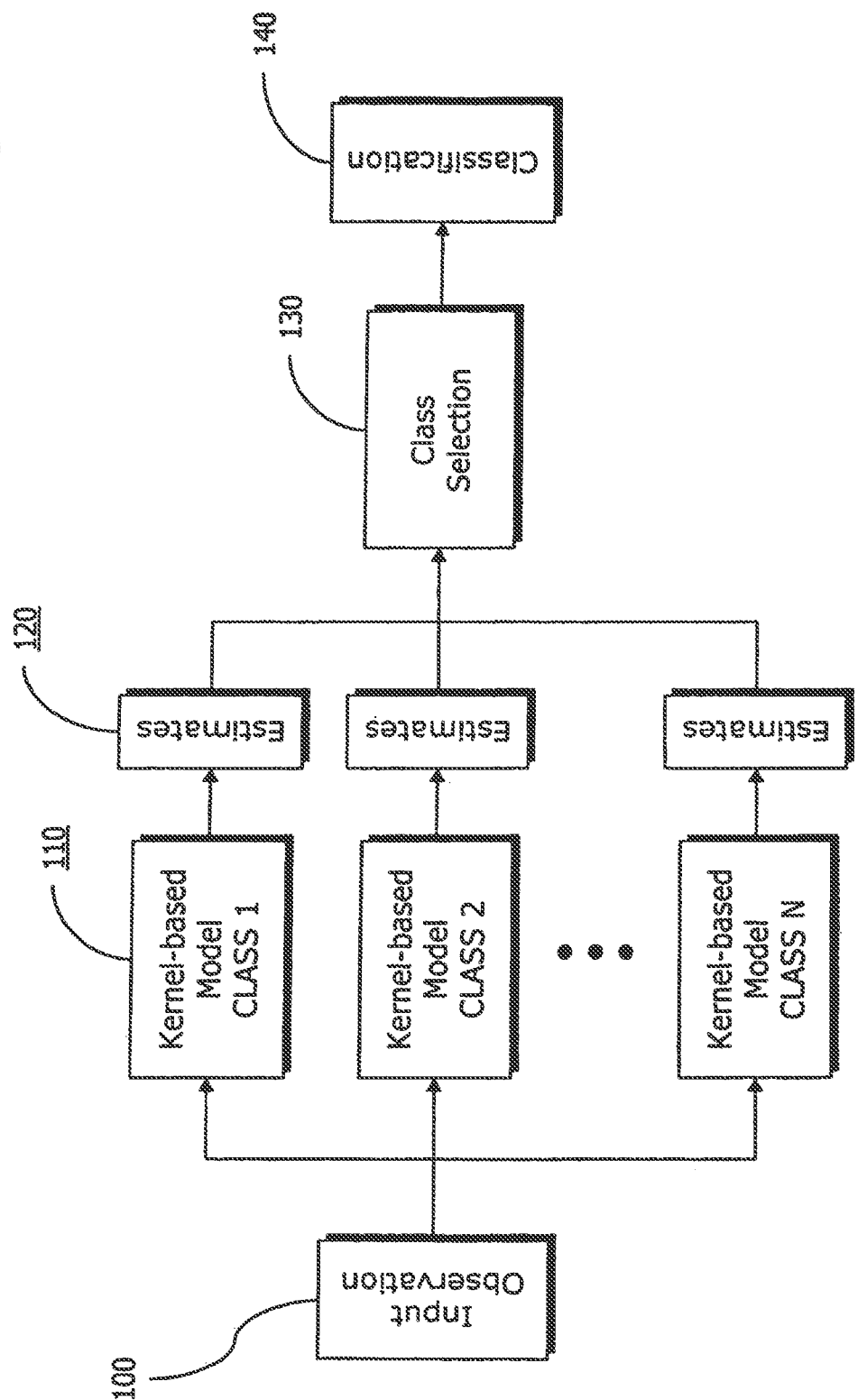
FIG. 1 shows a general arrangement for carrying out the present invention.

Turning to FIG. 1, the invention is generally shown to comprise the step of acquiring an input observation or set of observations 100, which may be provided by data collection technology well known in the art. A set of empirical, data driven, kernel-based models 110 process the input observation 100 to generate output estimates 120, which are then compared in a class selection step or module 130, to provide a classification 140 for the input. Each model 110 distinctly represents a given activity state or classification which it is desired to be able to classify the input with. For example, the activity states may be as simple as sleeping, awake-resting, awake-moving. As another example, it may be desirable to distinguish sitting-reading, sitting-watching, sitting-eating, and sitting-driving. Not all input observations need be classified as belonging to one of the classes represented by the models, as there is obviously a tremendous variety of human activity states, and only a very small subset may be of interest in any particular application.

As described above, the models 110 can be autoassociative estimators or inferential estimators. The models 110 can employ a kernel-based model comprising a set of learned vectors (or a transformation thereof), each vector comprising a set of sensor data values that are associated as a single observation. Every learned observation, or at least each of some subset of learned observations, may further be identified with a classification, for use in class selection. As an example, a typical observation as used to create the model and as measured as input to the system, could conceivably comprise a set of accelerometer readings (potentially in each axis of motion); a set of temperatures measured around the body; a heart rate reading; and an activity state identifier (e.g., "running" or "sleeping"). The dimensionality of the observations is not limited, and could be three sensor values or 100 sensor values. However, the set of sensor or feature data used to train each model should be the same format as the input observations (with the exception that the activity state class identifier is present only in the learned observations, and is predicted for the input observation).

Turning to the specifics of the model used to predict the class, the model can be either the autoassociative or inferential form of the general kernel-based estimator. The autoassociative form is generally:

$$x_{est} = \sum_{i=1}^{L} c_i K(x_{new}, x_i) \tag{1}$$

where the autoassociative estimate vector Xest is generated from a weighted sum of results from a kernel function K, which compares the input vector Xnew to learned patterns of expression levels, Xi. The learned patterns come from the class on which the model is trained. As mentioned above, the autoassociative form is used to generate an autoassociative estimate that is then compared for similarity to the input. In the inferential form:

$$y = \sum_{i=1}^{L} c_i K(x_{new}, x_i) \tag{2}$$

a class estimation variable y is predicted from the kernel-based comparison of the input $X_{new}$ to the learned observations. Each learned observation $X_i$ is associated with a class variable y, which are combined in a weighted fashion to predict y-hat.

Two forms of kernel-based modeling that can be used in the present invention are (a) kernel regression and (b) similarity-based modeling. An exemplary kernel regression is given by the Nadaraya-Watson kernel regression form:

$$y = \frac{\sum_{i=1}^{L} d_i^{out} K(x_{new}, d_i^{in})}{\sum_{i=1}^{L} K(x_{new}, d_i^{in})} = \frac{D_{out} \cdot (D_{in}^T \otimes x_{new})}{\sum (D_{in}^T \otimes x_{new})} \tag{3}$$

where $d_i$ are the learned vectors (referred to as Xi above), and D is the matrix of such vectors. The kernel is represented by the operator ⊗ in the second form of the equation above. In kernel regression, the weights c from equation 1 above are composed of the vectors of D normalized by the sum of the kernel comparison values. The learned observation matrix D has been split into two sections for the inferential form, the first Din being those elements of the multivariate observations corresponding to sensor data, and Dout being those elements corresponding to the classification assigned to the sensor data observations. Hence, with sensor readings in rows, and the last row being "class", and learning samples in columns, Din would be all rows above the last row, and Dout would be a vector of the last row, the class variable.

Alternatively, a similarity-based model (SBM) can be used. In the autoassociative form of the SBM modeling, the estimate generation module generates the autoassociative estimate of the input observation 100 by means of the following similarity-based calculation:

$$x_{est} = D \cdot (D^T \otimes D)^{-1} \cdot (D^T \otimes x_{in}) \tag{4}$$

where X(est) is the estimate vector, X(in) is the input observation, and D is a learned vector matrix comprising the set or subset of the learned observations in a model 110, and typically has columns corresponding to the number of observations and rows corresponding to number of data variables in each observation. The similarity operation or kernel is signified by the symbol ⊗, and has the general property of rendering a similarity score for the comparison of any two vectors from each of the operands. Thus the first term ($D^t \otimes D$) would yield a square matrix of values of size equal to the number of observations in D. The term ($D^t \otimes x_{in}$) would yield a vector of similarity values, one for each vector in D. This similarity operator is discussed in greater detail below.

The estimate can further be improved according to the following equation, where the estimate is normalized by dividing by the sum of the weights:

$$x_{est} = \frac{D \cdot (D^t \otimes D)^{-1} \cdot (D^t \otimes x_{in})}{\sum (D^t \otimes D)^{-1} \cdot (D^t \otimes x_{in})} \quad (5)$$

In the inferential form of similarity-based modeling, the output class y is estimated from the learned observations and the input according to:

$$y_{class} = D_{out} \cdot (D_{in}^t \otimes D_{in})^{-1} \cdot (D_{in}^T \otimes x_{in}) \quad (6)$$

or in the alternative preferred form with normalization:

$$y_{class} = \frac{D_{out} \cdot (D_{in}^T \otimes D_{in})^{-1} \cdot (D_{in}^T \otimes x_{in})}{\sum (D_{in}^T \otimes D_{in})^{-1} \cdot (D_{in}^T \otimes x_{in})} \quad (7)$$

The similarity operation or kernel generally provides a similarity score for the comparison of two identically-sized vectors, which similarity score:
1. Lies in a scalar range, the range being bounded at each end;
2. Has a value of one of the bounded ends, if the two vectors are identical;
3. Changes monotonically over the scalar range; and
4. Has an absolute value that increases as the two vectors approach being identical.

A wide variety of similarity operators are known in the art and may be used. For example, one similarity operator that can work in this fashion is the Euclidean distance between the two observation vectors in n-space, where n is the number of sensors or parameters in each vector.

One well-known kernel, by way of example, is the Epanechnikov kernel:

$$K_h(u) = \begin{cases} \frac{3}{4h}(1 - u^2/h^2); & |u| \leq h \\ 0; & |u| > h \end{cases} \quad (8)$$

where h is the bandwidth of the kernel, a tuning parameter, and u can be obtained from the difference between the current observation and the exemplar observations. Another well-known kernel that may be used according to the invention is the common Gaussian kernel:

$$K_h(x_{new}, x_i) = \frac{1}{\sqrt{2}} e^{\frac{-(x_{new}-x_i)^2}{2}} \quad (9)$$

The similarity operator may also be an "elemental" operator, which compares like elements from the two observation vectors to yield a similarity of the two values, and then the average is taken over all the similarities for all the elements in the observation vectors to produce an overall vector similarity score. One example of a similarity operator that can be used with the present invention returns a value between one (identical) and zero (dissimilar) provided by the minimum value of the two variable values divided by the maximum value. This is done for each variable element in the pair of vectors, and then the elemental similarities are averaged to provide the overall vector similarity. According to another similarity operator that can be used, an elemental similarity for like elements of two vectors is provided by:

$$s_c = \left(1 + \left(\frac{\theta_c^\lambda}{\rho}\right)\right)^{-1} \quad (10)$$

where $\theta_c$ (theta(c)) is a function of the elements A(c) and B(c) of any two vectors A and B respectively; $\lambda$ (lambda) and $\rho$ (rho) are sensitivity constants that can be selected for optimization. The function theta preferably returns a zero when the elements A(c) and B(c) are equal or identical, and preferably returns an increasingly large positive number with increasing difference of the two elements, with no limit. Lambda $\lambda$ and rho $\rho$ can be selected as any positive constants, and preferably are selected in the range of one to four. Theta can then be selected from a variety of functions according to the invention. Importantly, theta preferably scales the sameness or difference of two corresponding elements by the range observed over the reference library for the sensor corresponding to the two elements. By way of example, theta can be defined as follows:

$$\theta_c = \frac{\max(A_c, B_c) - \min(A_c, B_c)}{(\text{Max}_{range} - \text{Min}_{range})} \quad (11)$$

where:
$\text{Max}_{range}$ is the maximum value of the sensor corresponding to the cth element across all snapshots in the reference library D;
$\text{Min}_{range}$ is the minimum value of that sensor in the same manner;
$A_c$ represents the cth component of the snapshot A (typically the current live snapshot of data, but also can be a row or column from a matrix of snapshots);
$B_c$ represents the cth component of the snapshot B (typically a column of the reference library D, but can also be a vector or snapshot from any matrix of snapshots);

In an important alternative embodiment of the invention, both the inferential and autoassociative forms of the empirical kernel-based model can be generated "on-the-fly" based on qualities of the input observation, and drawing from a large set of learned observations, i.e., a reference set. This process is called localization. Accordingly, it is a preferred form of the invention that the above described calculations for the inferential and autoassociative forms can be carried out using a set of learned observations $x_i$ or $d_i$ that are selected from a larger set of reference observations, based on the input observation. Kernel-based models are exceptionally well suited for this kind of localization because they are trained in one pass and can be updated rapidly.

A variety of criteria can be used to constitute the localized D matrix membership, including the application of the similarity operator itself. Hence, according to one embodiment of the invention, the input observation can be compared to the reference library of learned observations, and a similarity s can be calculated for each comparison, identical to the "global similarity" discussed below with respect to equation 12. This provides a ranking of the reference observations vis-à-vis the input observation, and a certain top fraction of them can be included in the localized D matrix. As a further refinement of this localization aspect, vectors in the ranked list of all reference observations are included in localized D to the extent one of their component elements provides a value that "brackets" the corresponding value in the input vector, even if other observations have higher similarity to the input. This search down the ranked list is performed until either all values in the input vector are bracketed on both the low and high side by a value in one of the reference observations included in localized D, or until a maximum limit of vectors to include in D is reached, or until there are no further reference observations that have sufficiently high similarity to the input to surpass a similarity threshold for inclusion. Other slight modifications in determining the membership of localized D are within the scope of the invention.

Figure 2:
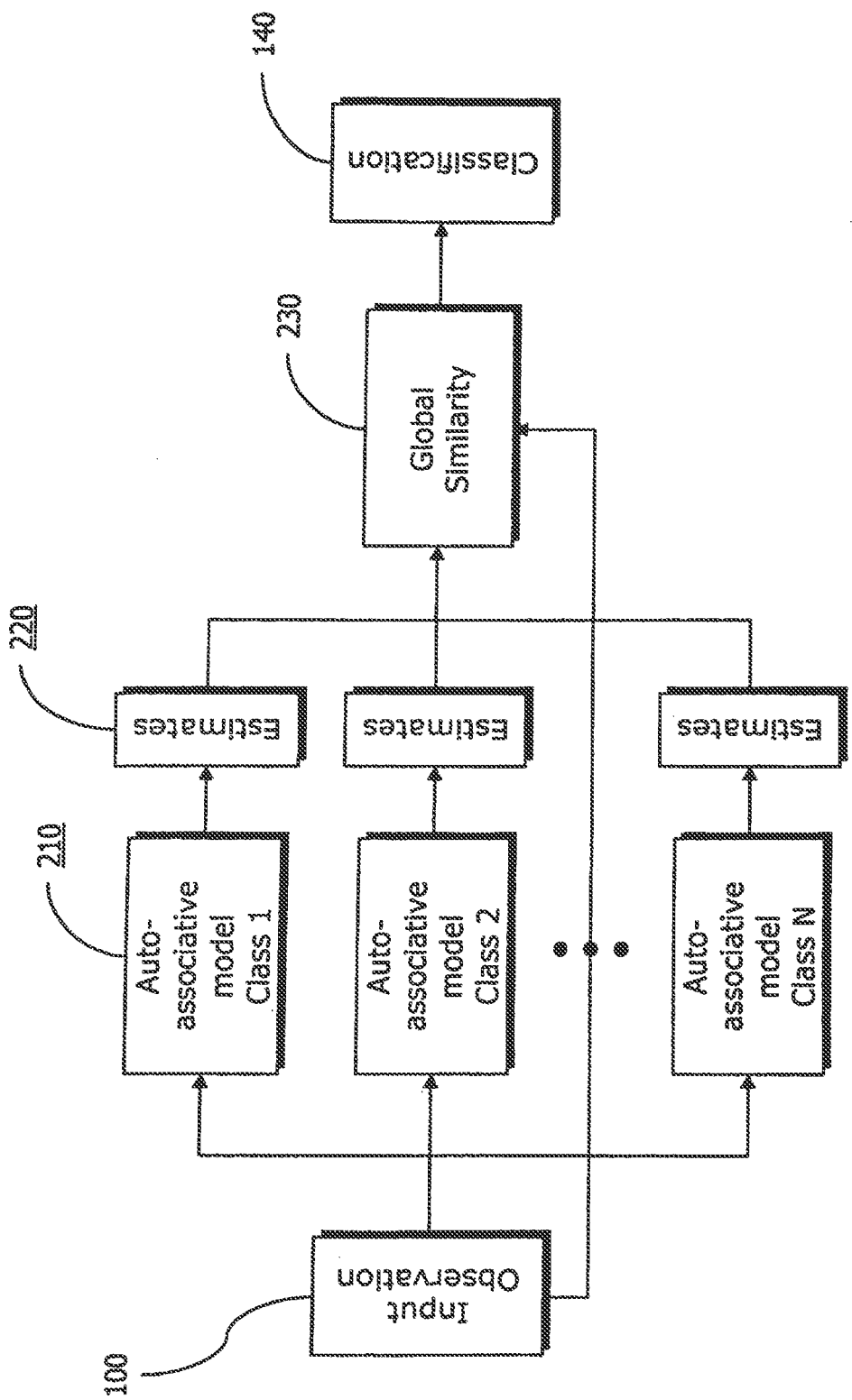
FIG. 2 shows a block diagram of the global similarity embodiment of the invention.

Turning now to FIG. 2, the autoassociative form of the activity state classifier of the present invention is shown to comprise a set of autoassociative kernel-based models 210, each of which corresponds to a class of activity. The estimates 220 from the models 210 comprise autoassociative estimates of at least some of the input variables comprising the input observation 100, and preferably all of the input variables. A comparison module 230 employs a "global similarity" function, which compares each estimate 220 to the input 100, using the similarity kernel function:

$$S_{global} = (x_{estimate}^t \otimes x_{in}) \quad (12)$$

where the kernel can be chosen from the above-described similarity operators. The resulting global similarity scores can then be compared, and the model with the highest global similarity score, i.e., the model class that most resembles the input observation, is designated the classification of the input observation. However, the global similarity from each model is preferably normalized so that the global similarities can be meaningfully compared. For example, one way is to normalize the global similarity from a model according to its general global similarity mean and variance for known classification in its class. This general mean and variance of the global similarity can be provided by doing leave-one-out modeling of the learned observations, for example. One class model may have typical global similarities at 0.97 mean and little variance, while the next maybe at 0.84 and large variance. The actual measured global similarity can be scaled to this mean and variance to provide a normalized score, which would then be used in the comparison to determine the class of the input. For example, the score can be the difference between the actual measured value and the mean, divided by the variance. Other calculations for normalizing are well known and can be used. For example, the distribution of general global similarity scores can be modeled with a kernel regression and the actual measured global similarity converted to a probability score related to how likely it is the measured similarity belongs to the distribution associated with that model.

Figure 3:
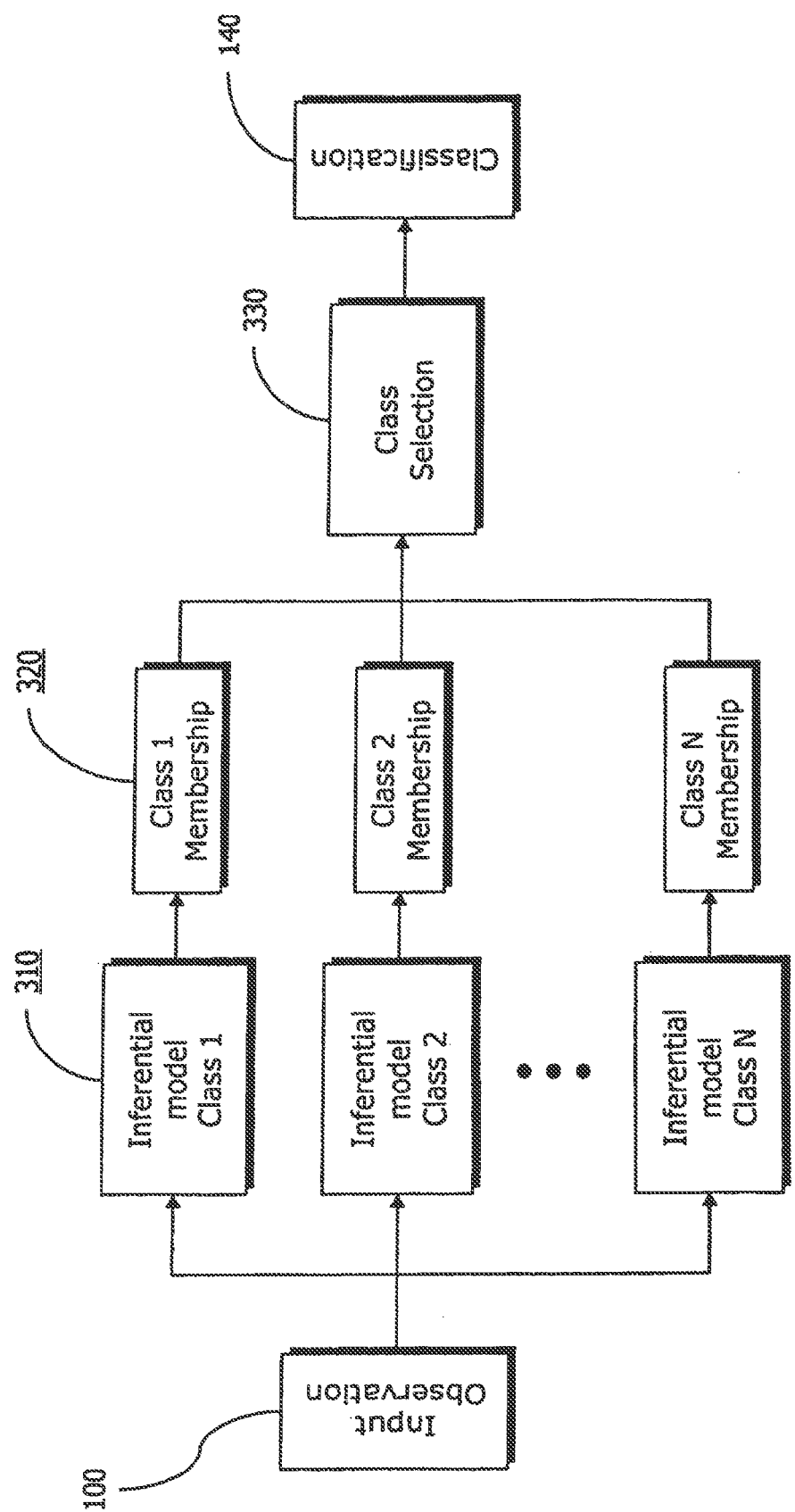
FIG. 3 shows a block diagram of the inferential embodiment of the invention.

The inferential form of the invention is depicted in FIG. 3, wherein is shown a set of inferential kernel-based models 310, each of which corresponds to an activity state classification. Each model 310 processes the input 100 to generate an estimate (y) of the degree of class membership 320, for example a value ranging from zero (input is not in class) to one (input is in class). This continuous membership value is then thresholded and rounded to the integer 1 or 0. A threshold may be also be used to return an "indecision" result, where the continuous membership value lies in a middle zone between 1 and 0. The class selection module 330 determines which class membership 320 prevails based on a count of thresholded classifications, and determines the classification 140.

Figure 4:
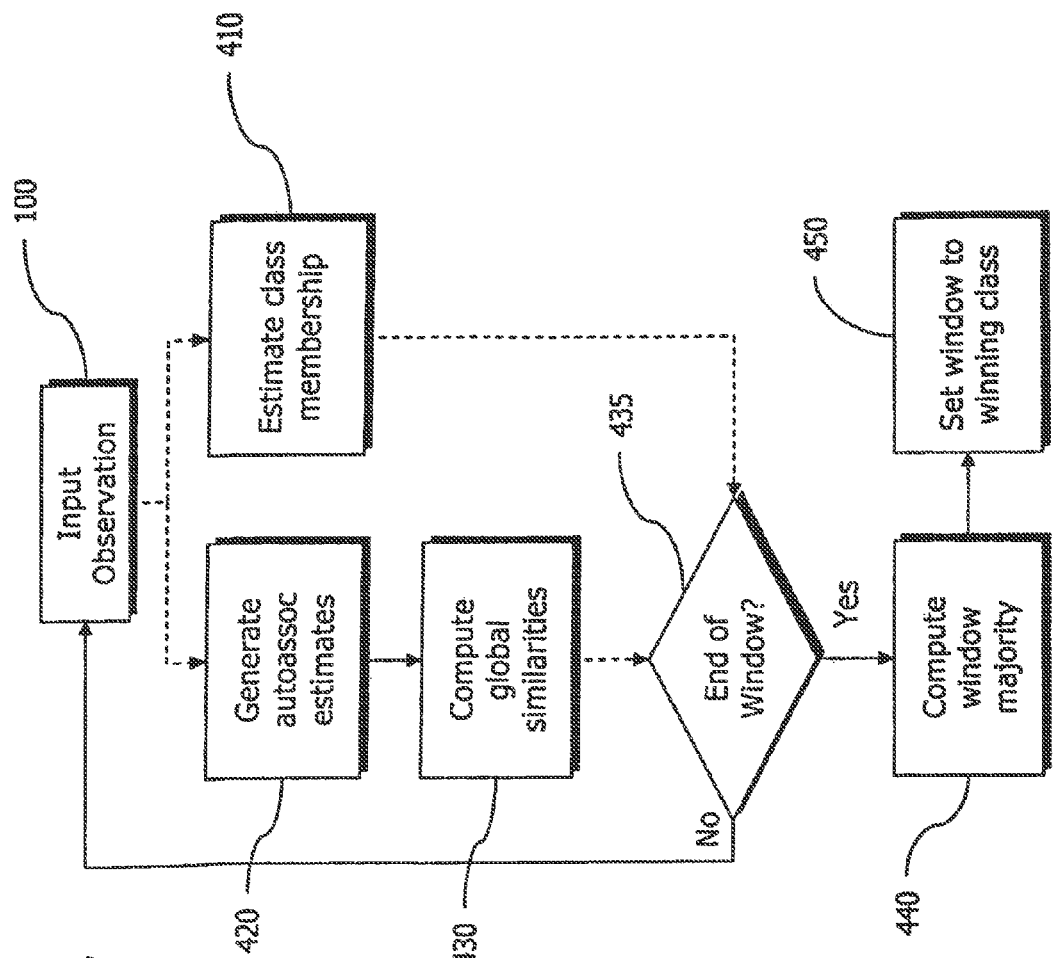
FIG. 4 shows a flowchart of a method for classifying sequences of observations according to the invention.

According to an important aspect of the invention, a methodology is shown in FIG. 4 to classifying activity state in the presence of particularly noisy or difficult to classify states, where instead of designating the activity state of each observation individually, a sequence of observations over a moving window is classified collectively. This can be done because activities of classification interest usually last a period of time, and depending on the data rate, usually extend to include several or many observations before the activity class changes. Accordingly, in step 100 an input observation is obtained, which can be processed optionally either by computing an autoassociative estimate in 420 and a global similarity in 430 for each class, or by computing the class membership inferentially in 410 for each class. In 435, a determination is made if further input observations remain to process in a window of observations, and if the window is not completely processed yet, the next observation is input 100. If all the observations in the window have been processed, then a statistical computation is made in 440 to determine which class had a majority or at least the highest number of times that it was the designated class for an observation in the window. This is then determined to be the class of all observations in the window in step 450, irrespective of whether some observations in that window seemed to belong to another classification in the course of processing steps 420, 430 or 440. The window of observations can be a sliding overlapped window, in which case, as the activity state of the person changes, the designation of some observations will be changed from an earlier determination to a later determination as that activity progresses and more observations from that new activity are processed.

An example of the invention's application follows:

EXAMPLE

A training data set was provided of almost 10,000 hours recorded every minute containing 16 fields for 2 user characteristic numbers, an annotation number for the activity being performed, gender number, 9 armband sensor values, user identification number, session number, and session time. The armband measured a variety of temperatures, conductivity of the skin, perspiration and the like, and was worn by test subjects throughout the day as they went about their activities. For purposes of testing and gauging the efficacy of the analysis, the test subjects also recorded separately their activity, choosing from a finite plurality of possible activities of interest in this test.

These data were first examined for anomalies and bandpass filters were applied to produce a filtered data set that was to be used to create the reference matrices (H) appropriate for modeling purposes. This filtering process removed about 1% of the original data. Users numbered 1, 2, 4, 5, 6, 9, 11, 13, 14, 15, 17, 18, 19, 20, 23, 25, 26, and 32 were available in the unfiltered training data set, however data for user 17 was completely absent in the filtered training data set so that data was not investigated further.

The objective was to distinguish and classify activity states designated by the annotation numbers 3004 and 5102, from amongst many activity states in the data. The annotation numbers designating class of activity in the training data set varied over a wide range and occurred with vastly different base rates: annotation 5102 comprised 16.97% of the filtered data while annotation 3004 comprised only 0.77%. The vectors that were known not to be annotation 5102 vectors included all annotations that were not 0, 2901, 2902, 3004, or 5103. Again, to accommodate such vastly different base rates, and to differentiate between annotations 5102 and 3004, the approach was taken to try to include in the annotation 5102 H model matrix approximately equal numbers of approximately equally spaced vectors from each user having annotation 3004, each user having annotation 5102, and each user not having annotations 0, 2901, 2902, 3004, or 5103, and an algorithm to achieve this was developed that produced an H matrix with about 3,000 vectors. Additionally, the vectors in the annotation 5102 H model matrix were restricted to be not too similar to each other, i.e., had global similarities below a threshold, a restriction that removed about 500 vectors. Class number 1 was assigned to all the annotation 5102 vectors and class number 0 was assigned to all vectors that did not have annotation 5102. A final set of 8 independent variables to model the annotation 5102 class number was chosen as characteristic 1, characteristic 2, and sensors 1, 2, 5, 6, 7, and 8.

The vectors that were known not to be annotation 3004 vectors included all annotations that were not 0, 3003, 3004, 5101, or 5199. Again, to accommodate vastly different base rates, and to differentiate between annotations 3004 and 5102, the approach was taken to try to include in the annotation 3004H matrix approximately equal numbers of approximately equally spaced vectors from each user having annotation 3004, each user having annotation 5102, and each user not having annotations 0, 3003, 3004, 5101, or 5199, and an algorithm to achieve this was developed that produced an H matrix with about 3,000 vectors. Additionally, the vectors in the annotation 3004 H matrix were restricted to be not too similar to each other, a restriction that removed about 500 vectors. Class number 1 was assigned to all the annotation 3004 vectors and class number 0 was assigned to all vectors that did not have annotation 3004. A final set of 9 independent variables to model the annotation 3004 class number was chosen as characteristic 1, characteristic 2, and sensors 1, 2, 3, 5, 6, 7, and 8.

The 580,264 vectors available in the unfiltered training data set were separately modeled with the appropriate H matrix and independent/dependent variables for class number for annotation 3004, and class number for annotation 5102 according to the inferential form of the similarity based model of equation 7 above. In this modeling process the local D matrices were limited to contain 10 vectors. These efforts produced a modeled class membership for annotation 3004, and a modeled class membership for annotation 5102 for each of the 580,264 vectors in the unfiltered training data set.

The modeled class memberships were all continuously variable, assuming values from a little less than 0 to a little more than 1. A moving window was applied to these continuous values according to the windowing method described with respect to FIG. 4, to assign integer values of 0 or 1 to blocks of vectors. A moving window approach requires several parameters to be defined and actions to be taken based on measurements of those parameters. A threshold above which the continuous numbers produce a count is first necessary. Window width and the acceptable fraction of the width for which these counts exist are also necessary. Finally the step size with which the window is moved over the data set must also be chosen. If an acceptable fraction of classifications occurs then an action is necessary to assign annotation integer numbers to particular vectors in the window. This window approach requires the data blocks to be separated by more than their widths. Note that for a window width of 1 the window method can reduce to the usual practice of rounding the continuously variable modeled gender number or class numbers.

The key base-rate-insensitive parameters that measure classification of a set of vectors are Sensitivity and Specificity. In this example, Sensitivity is defined as the fraction of the vectors of an actual class that have been predicted by modeling to belong to that class. Specificity is defined as the fraction of the vectors not actually of a class that also were predicted not to be in that class. The values of Sensitivity and Specificity are functions of four choices: 1) the threshold above which the continuous class membership numbers produce a count, 2) the window width, 3) the acceptable fraction of the window width for which counts exist, and 4) the action taken to assign integer modeled values to blocks of vectors. As a choice is varied, the values of Sensitivity and Specificity change and can be used to evaluate the effects of the choice on the classification. The four choices all have different, discrete effects on Sensitivity and Specificity. Choice 1 generally can be varied over its full range with Sensitivity having a maximum value of 1 at one end of the range and Specificity having a maximum value of 1 at the other end of the range. Choices 2, 3, and 4 generally cause Sensitivity and Specificity to achieve maxima somewhere near the middle of their acceptable ranges.

For choice 1, Sensitivity as a function of (1-Specificity) forms a receiver operating characteristic (ROC) curve that visually summarizes, quantitatively measures the accuracy of the classification methodology, and determines an optimal value for choice 1. Accuracy of a classification method is indicated by the area under the ROC curve. The optimum value for choice 1 is when the tangent to the ROC curve assumes a 45-degree angle. Before the 45-degree angle, any decrease in Specificity is more than made up for by an increase in Sensitivity while after the 45-degree angle the reverse is true. While choices 2, 3, and 4 do not exhibit the kind of behavior that make an ROC curve useful, one can still examine the effects of their variations on Sensitivity and Specificity and evaluate when any change in Specificity is more than made up for by the change in Sensitivity or vice-versa. The goal was to find a set of the four choices that produced the best tradeoff between Sensitivity and Specificity that was reasonably possible.

Basing all analysis choices on the tradeoffs between Sensitivity and Specificity for annotation 5102 resulted in quite good an area under the ROC curve of about 0.99. Based on a detailed analysis of the data, a value of 0.58 was chosen for the threshold above which continuous modeled class numbers produce a count. 98,172 of the 580,264 records in the unfiltered training data set are known have annotation 5102 while 73,668 records are known not to have annotation 5102. The methodology described herein correctly identified 96,288 and 72,251 of these records respectively. Including the unknown records, the methodology identified 173,759 or 30% of the 580,264 records in the unfiltered training data set that are consistent with having annotation 5102.

A similar analysis for annotation 3004 resulted in an area under the ROC curve of about 0.96. Based on a detailed analysis of the data, a value of 0.48 was chosen for the threshold above which continuous modeled class numbers produce a count. Only 4,413 of the 580,264 records in the unfiltered training data set actually have annotation 3004 while 167,368 records are known not to have annotation 3004. The methodology correctly identified 4,129 and 157, 993 of these records respectively. Including, the unknown records, the methodology identified 80,511 or 11% of the 580,264 records in the unfiltered training data set that are consistent with having annotation 3004.

The present invention can be implemented in a variety of computing platforms, and using a wide variety of sensor and attribute inputs. What is generally required is that the sensor data and attributes relate to the activity of the person, even if indirectly, and are captured contemporaneously, e.g., within the same period that they are similarly influenced by the activity state. A variety of measuring devices are being now commercialized by vendors, which generally contain the circuitry to capture and download data to a computer, by blue tooth, universal serial bus or other industry standard means. The present invention can be implemented as code that runs on these devices to provide classification of activity on-the-fly, or can be implemented as program code on a computer which receives downloads of the data from the device or devices. In the circumstance that the invention is implemented on a computer, data from several devices can be integrated in the analysis, provided time synchronization of the data from separate devices is made possible, e.g., by time stamping in each device. Data can naturally also be sent over the internet for processing at remote computing facilities, and results presented back via a web page.

It is conceived that the classification of activity state by the present invention can be used for purposes of filtering sensor data to select only that data that was gathered in certain activity states, for analysis, e.g., for medical diagnosis. An example might be to look at heart EKG data gathered from a person as they conducted their day, but only analyzing data when the person was in certain states of activity. The present invention provides the classification of the activity state which can be used to automatically select the data subsets from all the EKG data, for further analysis.

Another application of the invention is to perform timebase studies of activities of people where subjective estimates of activity duration and interval are not reliable.

In yet another application of the present invention, wearable hardware that gathers data and which has embedded code for processing the computations of the present invention can generate predictions of activity class, and when certain activity classes are realized, the hardware can initiate certain actions. For example, a driver can be monitored to look for changes in activity state which indicate the onset of sleep, and upon recognizing this state, an alarm is sounded to wake the driver up.

It will be appreciated by those skilled in the art, that modifications to the foregoing preferred embodiments may be made in various aspects. Other variations clearly would also work, and are within the scope and spirit of the invention. The present invention is set forth with particularity in the appended claims. It is deemed that the spirit and scope of that invention encompasses such modifications and alterations to the preferred embodiment as would be apparent to one of ordinary skill in the art and familiar with the teachings of the present application.

What is claimed:

1. A method for determining the class of an activity of a person, selected from a plurality of activities of interest, based on multivariate sensor data comprising values or features derived from values of sensors measuring physiological parameters from the person, comprising the steps of:

providing a plurality of kernel-based models, each corresponding to one of said activities of interest, and each model comprising a plurality of reference observations of said multivariate sensor data, at least some said reference observations having been acquired from sensors on a person during a modeled activity to which said model corresponds, and at least some said reference observations having been acquired from sensors on a person during activity different from that to which said model corresponds, and all said reference observations further having a class membership value corresponding to whether said reference observation is of said modeled activity of not;

obtaining a new observation of readings of said multivariate sensor data;

generating in a computer processor an inferential estimate of said class membership value for each of at least some of said kernel-based models using said new observation as input to the at least some of said kernel-based models, where said inferential estimate for a given kernel-based model is generated from a linear combination of at least some of said reference observations of said given kernel-based model; and determining the class of activity corresponding to said new observation based on a comparison of the class membership estimates.

2. A method according to claim 1, wherein at least one of said kernel-based models is a similarity-based model.

3. A method according to claim 2, further comprising the step of determining a class of activity of a window of successive observations in time to be the class most often represented among the successive observations.

4. A method according to claim 3, wherein said sensor data includes a measure of heart rate.

5. A method according to claim 3, wherein said sensor data includes a measure of temperature of the person.

6. A method according to claim 3, wherein said sensor data includes a measure of respiration.

7. A method according to claim 3, further comprising the step of filtering the window of successive observations as an input to a medical diagnosis based on the determination of the class of the window.

8. A method according to claim 3, wherein the computer processor used to generate the inferential estimate of said class membership value is embedded in a wearable hardware and further comprising the step of selectively initiating an action by said hardware upon determination of the class of activity corresponding to said window of successive observations.

9. A method according to claim 3, wherein said new observation is used to localize each said kernel-based model so that each said inferential estimate is generated from a linear combination of just a subset of reference observations of each said kernel-based model.

10. A method according to claim 9, wherein said subset is determined by a kernel-based similarity comparison of said new observation with said reference observations.

11. A method according to claim 10, wherein said kernel-based similarity comparison of said new observation with said reference observations marks for inclusion in said subset a predetermined number of those reference observations that have a highest similarity value when compared with said new observation.

12. A method according to claim 10, wherein said kernel-based similarity comparison of said new observation with said reference observations marks for inclusion in said subset those reference observations that have a similarity value above a predetermined threshold, and that further either have the highest similarity value with the new observation among a set of all reference observations that have a selected sensor data value less than the corresponding sensor data value of said new observation, or have the highest similarity value with the new observation among a set of all reference observations that have said selected sensor data value greater than the corresponding sensor data value of said new observation.

13. A method according to claim 1, wherein at least one of said kernel-based models is a kernel regression model.

14. A method according to claim 13, further comprising the step of determining a class of activity of a window of successive observations in time to be the class most often represented among the successive observations.

15. A method according to claim 14, wherein said sensor data includes a measure of heart rate.

16. A method according to claim 14, wherein said sensor data includes a measure of temperature of the person.

17. A method according to claim 14, wherein said sensor data includes a measure of respiration.

18. A method according to claim 1, further comprising the step of filtering said new observation as an input to a medical diagnosis based on the determination the class of activity.

19. A method according to claim 1, wherein the computer processor used to generate the inferential estimate of said class membership value is embedded in a wearable hardware and further comprising the step of selectively initiating an action by said hardware upon determination of the class of activity corresponding to said new observation.

* * * * *